Figure 1:
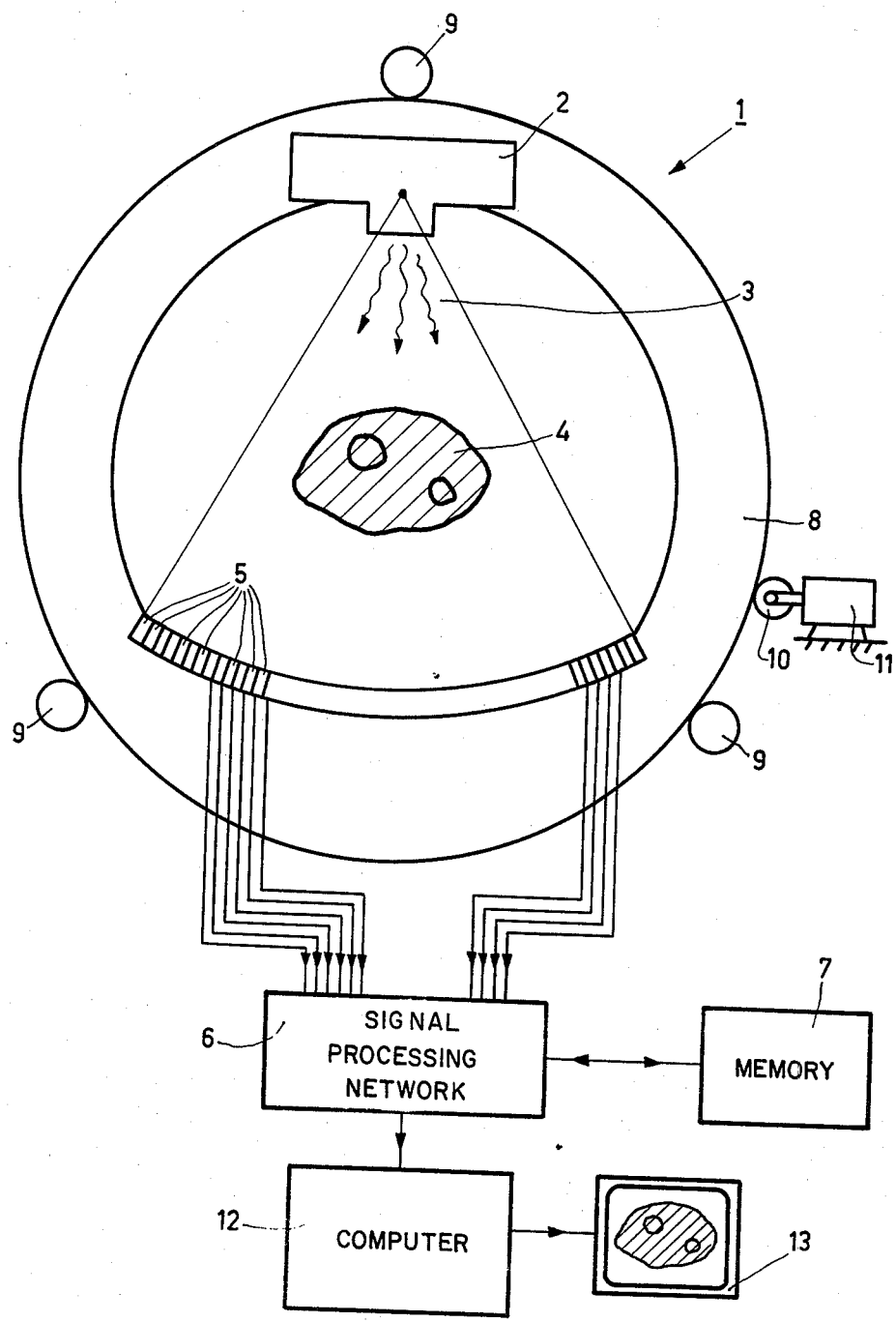

United States Patent [19]
Albrecht

[11] 4,225,789
[45] Sep. 30, 1980

[54] DEVICE FOR COMPUTER TOMOGRAPHY

[75] Inventor: Cornelius B. J. D. Albrecht, Eindhoven, Netherlands

[73] Assignee: U.S. Philips Corporation, New York, N.Y.

[21] Appl. No.: 938,268

[22] Filed: Aug. 30, 1978

[30] Foreign Application Priority Data

Sep. 14, 1977 [NL] Netherlands ......................... 7710052

[51] Int. Cl.² .......................... A61B 6/00; A61B 6/02; G01D 18/00; G12B 13/00
[52] U.S. Cl. ................................ 250/445 T; 250/252
[58] Field of Search ........................... 250/445 T, 252

[56] References Cited
U.S. PATENT DOCUMENTS

| | | | |
|---|---|---|---|
| 3,778,614 | 12/1973 | Hounsfield | 250/445 T |
| 3,965,358 | 6/1976 | Macovski | 250/445 T |
| 4,029,963 | 6/1977 | Alvarez et al. | 250/445 T |
| 4,035,647 | 7/1977 | Hounsfield et al. | 250/445 T |
| 4,124,799 | 11/1978 | Schittenhelm | 250/445 T |
| 4,149,081 | 4/1979 | Seppi | 250/445 T |

*Primary Examiner*—Alfred E. Smith
*Assistant Examiner*—T. N. Grigsby
*Attorney, Agent, or Firm*—Thomas A. Briody; Jack Oisher; Jack E. Haken

[57] ABSTRACT

A device for computer tomography, comprising an X-ray source, a number of X-ray detectors and a signal processing network which includes a comparator for comparing detector output signals with data obtained during measurement of a calibration material and stored in a memory. The comparator determines, by way of interpolation, the thicknesses of calibration material which correspond to detector output signals and provides computer input signals which are a function of these thicknesses. By means of these computer input signals, an image of the density distribution of an irradiated patient is calculated. This image is free from interference patterns caused by differences between the detectors, by non-linearity of the detectors or by hardening of the radiation.

8 Claims, 4 Drawing Figures

DEVICE FOR COMPUTER TOMOGRAPHY

The invention relates to a device for computed tomography, comprising an X-ray source for irradiating a patient to be examined, a number of X-ray detectors, and a signal processing network, including a memory, for processing detector output signals in order to form computer input signals.

A device of this kind is particularly suitable for X-ray diagnosis. During such an examination, a part of the body of a patient is irradiated from different directions, for example, by means of a flat fan-shaped beam. Locally transmitted radiation is measured and, from the measuring data thus obtained, the density distribution of the part of the body of the patient in the irradiated slice is calculated by means of a computer and, for example, displayed on a television monitor.

A device of the described kind is known from Netherlands Patent Application No. 76.02.700, in which the signal processing network comprises a circuit for at least partial corrections—by multiplication by correction factors stored in the memory—of differences between output signals of different detectors which are caused by local differences in the energy spectrum of the radiation in the beam. Errors in the calculation of the densities of the patient in the irradiated part which would be caused by these differences are thus counteracted.

In the described device, differences in the sensitivity of the individual detectors with respect to each other, non-linearity of the detectors and the changing of the energy spectrum—the "hardening"—of the X-radiation during the passage through human tissue are not taken into account. However, these phenomena may cause errors in the calculation of the densities of the patient which become manifest as disturbing interference patterns in the images.

The invention has for its object to eliminate this drawback. To this end, the device for computer tomography in accordance with the invention is characterized in that the signal processing network comprises a comparator for comparing measured detector output signals with detector output signals obtained during irradiation of a number of layer thicknesses of a calibration material having at least substantially the same X-ray absorption properties as human tissue and stored in the memory, in order to determine, by interpolation, a calibration value which is a function of the layer thickness of the calibration material corresponding to a measured detector output signal, and to generate a computer input signal which is a function of the determined calibration value. Each X-ray detector has the same spectral sensitivity during the examination as during the calibration, the X-radiation measured by each detector thus has the same spectral energy distribution. In accordance with the invention the calibration material has at least substantially the same X-ray absorption properties as human tissue. The calibration value determined by interpolation and the computer input signal derived therefrom are substantially independent of the sensitivity of the relevant detector, of the linearity of the relevant detector and of the hardening of the X-radiation during the passage through human tissue. Errors in the calculations which are liable to be caused thereby are thus counteracted to a degree which varies with the accuracy of the interpolation. It is to be noted that errors in the calculations caused by differences in the local energy spectrum of the radiation beam are also counteracted.

A simple device for computer tomography in accordance with the invention is characterized in that the detector output signals stored in the memory are obtained by irradiation of a number of plates of a synthetic material which are shaped as concentric sectors of a sphere whose mathematical centres are situated within the X-ray source. The plates of synthetic material are preferably made of methyl methacrylate. As a result of the choice of the shape of the plates of synthetic material the irradiated thickness is equal to the actual thickness. The detector output signals obtained during calibration can thus be readily applied to the memory.

A preferred embodiment of the device for computer tomography in accordance with the invention comprises an X-ray detector which is adapted to supply an output signal for the continuous adaptation of the detector output signals stored in the memory to the instantaneous value of the radiation output power of the X-ray source. As a result, the occurrence of errors in the calculations due to drift of said power is counteracted.

From Netherlands Patent Application No. 75.03.520 it is known to measure the radiation output power of the X-ray source continuously by means of an additional detector, and to use the data so obtained to counteract errors in the calculations which are caused by drift of said power. In contrast, in the device in accordance with the invention, however, this detector supplies an output signal which is used for performing operations on the output signals of all other detectors such that they are rendered insensitive to drift of the radiation output power of the X-ray source. To this end, the output signals of all detectors are divided by the output signal of the additional detector.

A further preferred embodiment of the device for computer tomography in accordance with the invention is characterized in that it comprises two X-ray detectors which have a different spectral sensitivity with respect to each other and which are intended to supply output signals for the continuous adaptation of the detector output signals stored in the memory to the instantaneous value of the high voltage and the current of an X-ray source which is constructed as an X-ray tube. As a result, errors in the calculations, caused by drift of the high voltage and the current, are counteracted.

The invention will be described in detail hereinafter, by way of example, with reference to the accompanying drawing.

Figure 2:
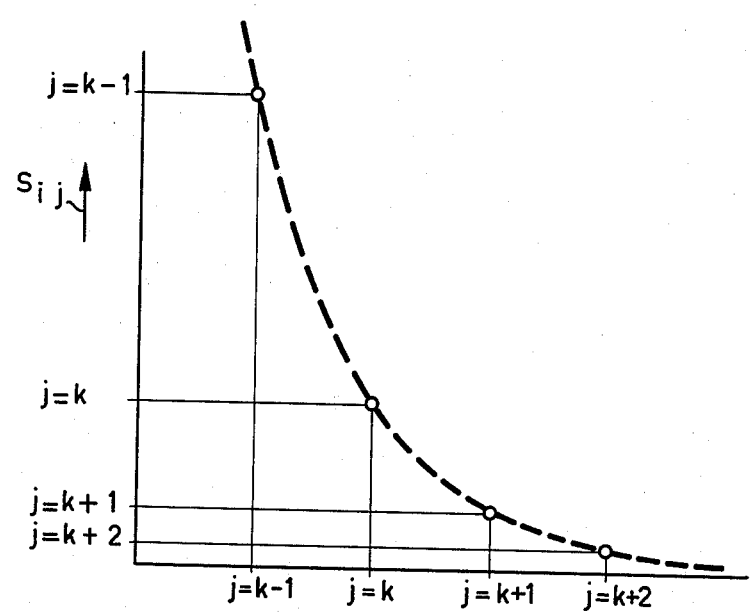
Figure 3:
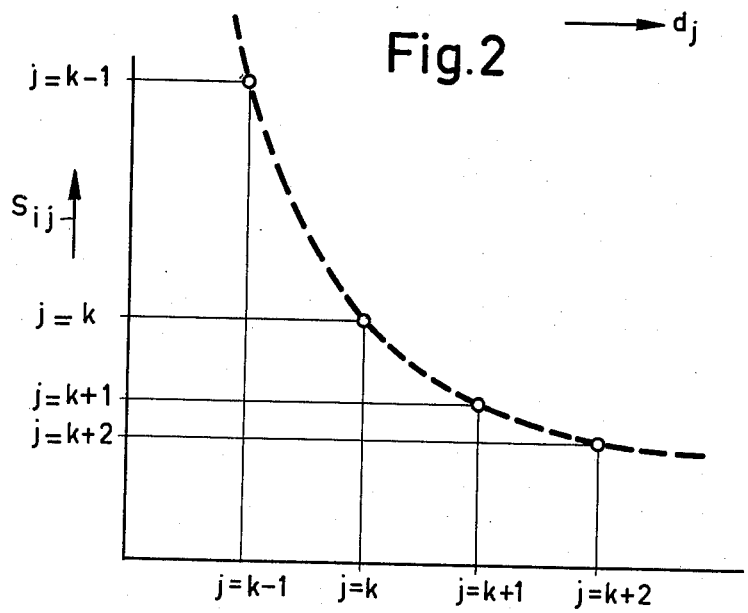
Figure 4:
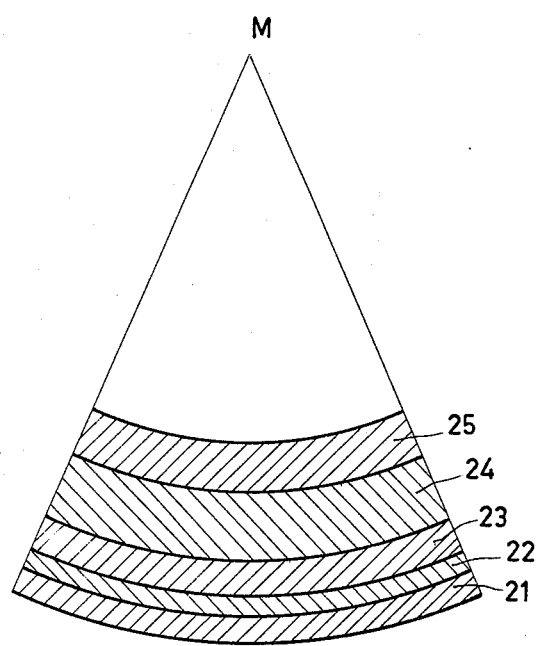

FIG. 1 diagrammatically shows a device for computer tomography in accordance with the invention, FIGS. 2 and 3 are a graphic representation of calibration data stored in a memory, and FIG. 4 is a diagrammatic sectional view of plates of synthetic material for calibration which are stacked one on top of the other.

FIG. 1 shows a device for computer tomography 1, in which a part of the body 4 of a patient to be examined is irradiated by an X-ray beam 3 which is generated by an X-ray source 2. The X-ray source 2 is formed, for example, by an X-ray tube comprising a tungsten rotary anode whereby radiation having an energy of from 80 to 150 keV is generated. The X-ray beam subtends an angle of, for example, 60° in the plane of the drawing and has a thickness of, for example 15 mm in the perpendicular direction. In order to enable an examination to be quickly performed, the transmitted radiation is measured by means of a large number of X-ray detectors 5 which are arranged on a circle. The X-ray detectors 5 are connected to a signal processing network 6, comprising a memory 7, for processing detector output signals in order to form computer input signals. In order to obtain an adequate number of measuring data, the X-ray beam is rotated around the patient, together with the detector, during the examination. To this end, the X-ray source 2 and the X-ray detectors 5 are mounted on a ring which is journalled on wheels 9 and which can be rotated around the patient 4 by means of a drive 10 which includes a motor 11. Using a computer 12, the density distribution of the part of the body examined is calculated and, for example, displayed on a television monitor 13 for evaluation.

The detector output signal $S_i$ of the $i^{th}$ X-ray detector of the circular array is inter alia determined by:
- the spectral sensitivity of the $i^{th}$ X-ray detector,
- the linearity of the $i^{th}$ X-ray detector,
- the spectral energy distribution of the radiation transmitted by the X-ray source in the direction of the $i^{th}$ detector,
- the degree of hardening of the X-radiation during the passage of human tissue between the X-ray source and the $i^{th}$ detector, and
- the spectral dependence of the absorption coefficient of human tissue.

If one or more of these factors deviates for different detectors, errors are liable to occur in the calculation of the densities of the patient. These errors are manifested as disturbing interference patterns in the image. In accordance with the invention, during the calibration of the device the spectral sensitivity of the detectors, the linearity of the detectors and the spectral energy distribution of the radiation transmitted by the X-ray source are equal to those during an examination. The calibration material has substantially the same X-ray absorption properties as human so that the degree of hardening of the radiation by the irradiated medium and the spectral dependency of the absorption coefficient of the irradiated medium during calibration are substantially equal to those during an examination. During an examination, the output signals of the $i^{th}$ detector are compared with calibration data stored in the memory for the $i^{th}$ detector and, using an interpolation yet to be described, a calibration value is determined which is a function of the calibration material thickness corresponding to the detector output signal. The computer input signals thus generated are a function of the calibration value. These signals, and hence the further calculations and the images, are independent of the said factors which determine the detector output signal. Disturbing interference patterns in the image are thus counteracted.

Hereinafter, a description will be given of two interpolation methods for determining a calibration value which is a function of the thickness d of a layer of calibration material corresponding to an arbitrary detector output signal $S_i$.

According to the first method, the calibration value equals the thickness d of the layer of calibration material itself. FIG. 2 is a graphic representation of calibration data of the $i^{th}$ detector as stored in the memory 7 of FIG. 1 in accordance with the first method. $S_{ij}$, represents the detector output signal of the $i^{th}$ detector, measured with a layer of calibration material having a thickness $d_j$. When, during an examination the $i^{th}$ detector supplies an output signal $S_i$ whose value lies between those of the calibration measurements $S_{i\,k}$ and $S_{i\,k+1}$, an associated calibration value d is derived therefrom by the following interpolation operation:

$$d = d_k + \frac{\log S_i - \log S_{ik}}{\log S_{ik+1} - \log S_{ik}} (d_{k+1} - d_k)$$

because, $$d = d_k + \frac{d - d_k}{d_{k+1} - d_k} (d_{k+1} - d_k):$$

and because, as is denoted by a broken line in FIG. 2, in first approximation:

$$\log S_i = \text{constant} \cdot d$$

because for the transmission T of radiation, whereto $S_i$ is proportional, through a layer having an absorption coefficient $\mu$ and a thickness d:

$$T = \exp. (-\mu \cdot d).$$

According to the second method, the calibration value is a function D of the thickness d of the layer of calibration material, for which:

$$D = \exp. (\bar{\mu} \cdot d)$$

in which $\bar{\mu}$ represents the mean absorption coefficient, for the X-radiation used, of human tissue.

FIG. 3 is a graphic representation of calibration data of the $i^{th}$ detector as stored in the memory 7 of FIG. 1 according to the second interpolation method. $S_{ij}$ is the detector output signal of the $i^{th}$ detector, measured for a layer of calibration material having a thickness $d_j$. $D_j$ is the calibration value calculated according to the above formula for a thickness $d_j$. If the $i^{th}$ detector supplies an output signal $S_i$ during an examination whose value lies between those of the calibration measurements $S_{i\,k}$ and $S_{i\,k+1}$, an associated calibration value D is derived therefrom by the following interpolation operation:

$$D = D_k + \frac{S_i^{-1} - S_i^{-1}{}_k}{S_i^{-1}{}_{k+1} - S_i^{-1}{}_k} \cdot (D_{k+1} - D_k)$$

because:

$$D = D_k + \frac{D - D_k}{D_{k+1} - D_k} \cdot (D_{k+1} - D_k)$$

and because, as is denoted by a broken line in FIG. 3, in a first approximation:

$$S_i \cdot D = \text{constant},$$

because for the transmission T of radiation, whereto $S_i$ is proportional, through a layer having an absorption coefficient $\bar{\mu}$ and a thickness d:

$$T = \exp. (-\bar{\mu} \cdot d) = D^{-1}.$$

It is to be noted that higher-order interpolations can also be used.

Moreover, using interpolations as described above, accurate tables of values of $S_i$ and associated calibration values d and D, respectively, can be calculated. If the $i^{th}$ detector then supplies a value $S_i$ during an examination, an associated calibration value d or D can then be looked up in the relevant table.

It is also to be noted that for both of said interpolation methods a computer input signal can be derived from the calculated calibration values, said signal being proportional to d or to $D = \exp(\bar{\mu} \cdot d)$.

FIG. 4 is a diagrammatic sectional view of five plates 21 ... 25 of synthetic material which are arranged one on top of the other and which are shaped as sectors of a sphere. When the device for computer tomography shown in FIG. 1 is calibrated, the common center M of the sectors of a sphere is situated inside the X-ray source 2 and the plates 21 ... 25 are arranged in place of the patient 4. The radiation in the X-ray beam 3 is then incident at right angles all across the plates 21 ... 25, so that the irradiated thickness equals the actual thickness of the plates. The data obtained by calibration may, therefore, be readily applied to the memory 7. The plates 21 ... 25 are preferably made of perspex (methyl methacrylate).

The occurrence of errors in the calculations, caused by drift of the radiation output power of the X-ray source, is counteracted by continuously adapting the data determined by calibration and stored in the memory 7, graphically shown in FIGS. 2 and 3, to this power. The output signal $S_i$ of the $i^{th}$ detector of the array of detectors arranged on a circle is a function $h_i(W)$ of the radiation output power W of the X-ray source. The value of $S_{ij}$ which corresponds to a layer of calibration material having a thickness $d_j$ at any instant may, therefore, be written in a first approximation as follows:

$$S_{ij} = S_{ij}^o + \left( \frac{\partial h_{ij}(W)}{\partial W} \right)_o (W - W^o).$$

in which the indices "o" denote the values determined by calibration. When W is continuously measured, by means of an additional detector in accordance with the invention, the data stored in the memory 7 can be continuously adapted in the described manner. When the device for computer tomography is calibrated, therefore, not only the data shown in the FIGS. 2 or 3 must be stored in the memory 7, but also the radiation output power of the X-ray source $W^o$ and $$\left( \frac{\partial h_{ij}(W)}{\partial W} \right)_o.$$

The latter value is determined by performing two calibration measurements for each plate thickness of calibration material $d_j$, i.e. for the radiation output powers $W^o$ and $W^o + \Delta$, where $\Delta << W$. The required value then follows from the equations:

$$S_{ij}(W = W^o) = S_{ij}^o$$

$$S_{ij}(W = W^o + \Delta) = S_{ij}^o + \left( \frac{\partial h_{ij}(W)}{\partial W} \right)_o \cdot \Delta$$

The occurrence of errors in the calculations caused by drift of the high voltage and the current are counteracted by continuously adapting the data determined by calibration and stored in the memory 7, graphically shown in FIG. 2 or FIG. 3, to the high voltage and the current of the X-ray tube 2 (see FIG. 1). The output signal $S_i$ of the $i^{th}$ detector of the array of detectors is a function $f_i(V, I)$ of the high voltage V and the current I of the X-ray tube. The value of $S_{ij}$ which corresponds to a layer of calibration material having a thickness $d_j$ at any instant may, therefore, be written in a first approximation as follows:

$$S_{ij} = S_{ij}^o + \left( \frac{\partial f_{ij}(V,I)}{\partial V} \right)_o \cdot (V - V^o) + \left( \frac{\partial f_{ij}(V,I)}{\partial I} \right)_o \cdot (I - I^o),$$

in which the indices "0" denote values determined during calibration. The data stored in the memory 7 can be continuously adapted by continuously measuring V and I in the described manner, by means of two additional detectors yet to be described in accordance with the invention. To this end, during calibration of the device for computer tomography not only the data shown in FIG. 2 or FIG. 3 must be stored in the memory 7, but also the high voltage $V^o$, the current $I^o$ and the values $$\left( \frac{\partial f_{ij}(V,I)}{\partial V} \right)_o$$

and $$\left( \frac{\partial f_{ij}(V,I)}{\partial I} \right)_o$$

The latter values are determined by performing three calibration measurements for each plate thickness of calibration material $d_j$, i.e. at the following X-ray tube settings: $V^o$, $I^o$; $V^o + \Delta V$, $I^o$ and $V^o$, $I^o + \Delta I$, where $\Delta V << V^o$ and $\Delta I << I^o$. The required values then follow from the equations:

$$S_{ij}(V^o, I^o) = S_{ij}^o.$$

$$S_{ij}(V^o + \Delta V, I^o) = S_{ij}^o + \left( \frac{\partial f_{ij}(V,I)}{\partial V} \right)_o \cdot \Delta V$$

$$S_{ij}(V^o, I^o + \Delta I) = S_{ij}^o + \left( \frac{\partial f_{ij}(V,I)}{\partial I} \right)_o \cdot \Delta I$$

The high voltage V and the current I are measured in accordance with the invention by means of two X-ray detectors having a different spectral sensitivity. When the radiation is measured from an X-ray tube comprising a tungsten rotary anode whereby X-radiation having an energy of from 80 to 150 keV is generated, the following generally holds good for the output signal R of an X-ray detector:

$$R = \text{constant} \cdot I^\alpha \cdot V^\beta$$

in which the exponents $\alpha$ and $\beta$ are dependent of the energy spectrum of the radiation absorbed and hence measured by the detector. For a scintillation detector comprising an NaI crystal having a thickness of 1 mm, absorbing mainly soft radiation, for example, $\alpha$ and $\beta$ are approximately 1 and 3, respectively. For a scintillation detector comprising an NaJ crystal having a thickness of 10 mm, measuring radiation via a copper filter havng a thickness of 5 mm so that it absorbs mainly hard radiation, $\alpha$ and $\beta$ are approximately 1 and 6, respectively. When the different detectors are denoted by the indices "1" and "2":

$$R_1 = k_1 \cdot I^{\alpha_1} \cdot V^{\beta_1} \quad (k_1: \text{constant})$$

and $$R_2 = k_2 \cdot I^{\alpha_2} \cdot V^{\beta_2} \quad (k_2: \text{constant}).$$

V and I can be determined from these two equations, and hence also the two measurements.

In a different approach it is directly assumed that the output signal $S_i$ of the $i^{th}$ detector of the array of detectors is a function $g_i(R_1, R_2)$ of the two output signals $R_1$ and $R_2$ of the additional detectors whereby the high voltage V and the current I of the X-ray tube are measured. The value of $S_{ij}$ which at any instant corresponds to a layer of calibration material having a thickness $d_j$ can be written in a first approximation as:

$$S_{ij} = S_{ij}^o + \left(\frac{\partial g_{ij}(R_1, R_2)}{\partial R_1}\right)_o \cdot (R_1 - R_1^o) + \left(\frac{\partial g_{ij}(R_1, R_2)}{\partial R_2}\right)_o \cdot (R_2 - R_2^o)$$

in which the indices "0" denote values determined during calibration. The data stored in the memory 7 can be continuously adapted to the instantaneous values of the high voltage V and the current I of the X-ray tube by continuously measuring $R_1$ and $R_2$. To this end, when the device for computer tomography is calibrated, not only the data shown in FIG. 2 should be stored in the memory 7, but also the values $R_1^o$, $R_2^o$ and the values $$\left(\frac{\partial g_{ij}(R_1, R_2)}{\partial R_1}\right)_o$$

and $$\left(\frac{\partial g_{ij}(R_1, R_2)}{\partial R_2}\right)_o$$

The latter values are determined by performing three calibration measurements for each plate thickness of calibration material $d_j$, i.e. at the following X-ray tube settings:

$V^o$, $I^o$; $V^o + \Delta V$, $I^o$ and $V^o$, $I^o + \Delta I$, where $\Delta V << V^o$ and $\Delta I << I^o$.

The required values then follow from the equations:

$$S_{ij}(V^o, I^o) = S_{ij}^o$$
$$S_{ij}(V^o + \Delta V, I^o) = S_{ij}^o + \left(\frac{\partial g_{ij}(R_1, R_2)}{\partial R_1}\right)_o \cdot (R_1(V^o + \Delta V, I^o) - R_1^o) + \left(\frac{\partial g_{ij}(R_1, R_2)}{\partial R_2}\right)_o \cdot (R_2(V^o + \Delta V, I^o) - R_2^o).$$
$$S_{ij}(V^o, I^o + \Delta I) = S_{ij}^o + \left(\frac{\partial g_{ij}(R_1, R_2)}{\partial R_1}\right)_o \cdot (R_1(V^o, I^o + \Delta I) - R_1^o) +$$

-continued
$$\left(\frac{\partial g_{ij}(R_1, R_2)}{\partial R_2}\right)_o \cdot (R_2(V^o, I^o + \Delta I) - R_2^o).$$

It is to be noted that, if the X-ray tube is sufficiently stable as regards one of the parameters V and I, the adaptation of the data shown in FIG. 2 may be limited to the continuous adaptation to the value of the other parameter. The method is then directly comparable with that for the adaptation to the radiation output power of the X-ray tube.

What is claimed is:

1. A device for computed tomography examinations comprising:
   X-ray source means which irradiate a patient position from different directions;
   a plurality of X-ray detectors; and
   signal processing network means, including a memory, which process output signals from the detectors to form computer input signals, the signal processing network means including comparator means which function to compare a first group of output signals from the detectors, which are obtained during examination of a patient with a second group of output signals from the detectors, which are obtained during radiation of a number of layer thicknesses of a calibration material, the second group being stored in the memory, the calibration material having substantially the same X-ray absorption properties as human tissue, the network means functioning to determine, by interpolation, a calibration value which is a function of the layer thickness of the calibration material which corresponds to a measured output signal in the second group and to generate a computer input signal which is a function of the determined calibration value.

2. A device as claimed in claim 1 wherein the calibration material is a synthetic material, shaped as concentric sectors of a sphere, which sphere is centered within the X-ray source means.

3. A device as claimed in claim 2 wherein the synthetic material is methyl methacrylate.

4. A device as claimed in claims 1, 2 or 3 further comprising
   a pair of additional X-ray detectors which have different spectral sensitivities with respect to each other and which supply output signals to the signal processing network;
   wherein the X-ray source means comprise an X-ray tube; and
   wherein the signal processing network further functions to modify the computer input signal as a function of the values of the output signals from the detector pair and of a high voltage and current applied to the X-ray tube.

5. A device as claimed in claim 4 wherein the detector pair comprises a first scintillation crystal having a thickness of approximately 1 millimeter, a second scintillation crystal having a thickness of approximately 5 millimeters, and a filter, comprising materials selected from the group consisting of copper and brass, disposed to shield said second scintillation crystal.

6. A device as claimed in any of the preceding claims further comprising means which monitor the output power of the X-ray source means and which supply a third group of output signals characteristic thereof, and wherein the signal processing network means further function to modify the value of the computer input signal as a function of the values of the third group of signals.

7. A device as claimed in claim 6 further comprising a pair of additional X-ray detectors which have different spectral sensitivities with respect to each other and which supply output signals to the signal processing network;

wherein the X-ray source means comprise an X-ray tube; and wherein the signal processing network further functions to modify the computer input signal as a function of the values of the output signals from the detector pair and of a high voltage and current applied to the X-ray tube.

8. A device as claimed in claim 7 wherein the detector pair comprises a first scintillation crystal having a thickness of approximately 1 millimeter, a second scintillation crystal having a thickness of approximately 5 millimeters, and a filter, comprising materials selected from the group consisting of copper and brass, disposed to shield said second scintillation crystal.

* * * * *